(12) United States Patent
Bayat

(10) Patent No.: US 8,012,089 B2
(45) Date of Patent: Sep. 6, 2011

(54) DISPOSABLE EXPANDABLE CORDLESS LIGHTED RETRACTOR

(76) Inventor: Ardeshir Bayat, Chestar (GB)

( * ) Notice: Subject to any disclaimer, the term of this patent is extended or adjusted under 35 U.S.C. 154(b) by 910 days.

(21) Appl. No.: 12/006,870

(22) Filed: Jan. 7, 2008

(65) Prior Publication Data

US 2008/0108877 A1   May 8, 2008

Related U.S. Application Data

(63) Continuation-in-part of application No. 11/439,316, filed on May 22, 2006, now Pat. No. 7,384,392.

(51) Int. Cl.
*A61B 1/32* (2006.01)
(52) U.S. Cl. .......................................................... 600/214
(58) Field of Classification Search ........... 600/201–246
See application file for complete search history.

(56) References Cited

U.S. PATENT DOCUMENTS

| 2,296,793 | A |   | 9/1942 | Krischbaum |  |
|---|---|---|---|---|---|
| 3,638,644 | A | * | 2/1972 | Reick | 600/191 |
| 3,716,047 | A |   | 2/1973 | Moore et al. |  |
| 4,052,980 | A |   | 10/1977 | Grams et al. |  |
| 4,337,763 | A | * | 7/1982 | Petrassevich | 600/210 |
| 4,562,832 | A |   | 1/1986 | Wilder et al. |  |
| 5,339,801 | A | * | 8/1994 | Poloyko et al. | 600/214 |
| 5,722,935 | A | * | 3/1998 | Christian | 600/214 |
| 5,967,971 | A |   | 10/1999 | Bolser |  |
| 6,080,105 | A |   | 6/2000 | Spears |  |
| 6,322,500 | B1 | * | 11/2001 | Sikora et al. | 600/219 |
| 6,504,985 | B2 | * | 1/2003 | Parker et al. | 385/133 |
| 6,591,049 | B2 | * | 7/2003 | Williams et al. | 385/123 |
| 6,602,188 | B2 |   | 8/2003 | Bolser |  |
| 2003/0095781 | A1 | * | 5/2003 | Williams | 385/146 |
| 2008/0108877 | A1 | * | 5/2008 | Bayat | 600/214 |

FOREIGN PATENT DOCUMENTS

WO   WO 2004/077922   9/2004

* cited by examiner

*Primary Examiner* — Thomas C. Barrett
*Assistant Examiner* — Christopher Beccia
(74) *Attorney, Agent, or Firm* — Cislo & Thomas, LLP

(57) ABSTRACT

A hand-held, surgical instrument to manipulate a patient's tissues having a grip, a first blade, a second blade, a blade actuator, at least one blade rib, a light, and a power source. The first blade and the second blade each extend from the base end of the grip. The second blade is divided longitudinally into a left segment and a right segment, which are each pivotable about a common axis. Movement of the blade actuator causes the segments of the second blade to pivot about the common axis. The light illuminates the patient's tissues proximate the blades. The device may include suction ports on the underside of the first blade to provide aspiration. The blade rib may include multiple longitudinal blade ribs extending along the length of the first blade, the second blade, or both. The blade rib may also include multiple transverse blade ribs extending along the width of the first blade, the second blade, or both. The device may also include an integral camera and wireless transmitter to provide images of the patient's tissues to a separate display.

2 Claims, 5 Drawing Sheets

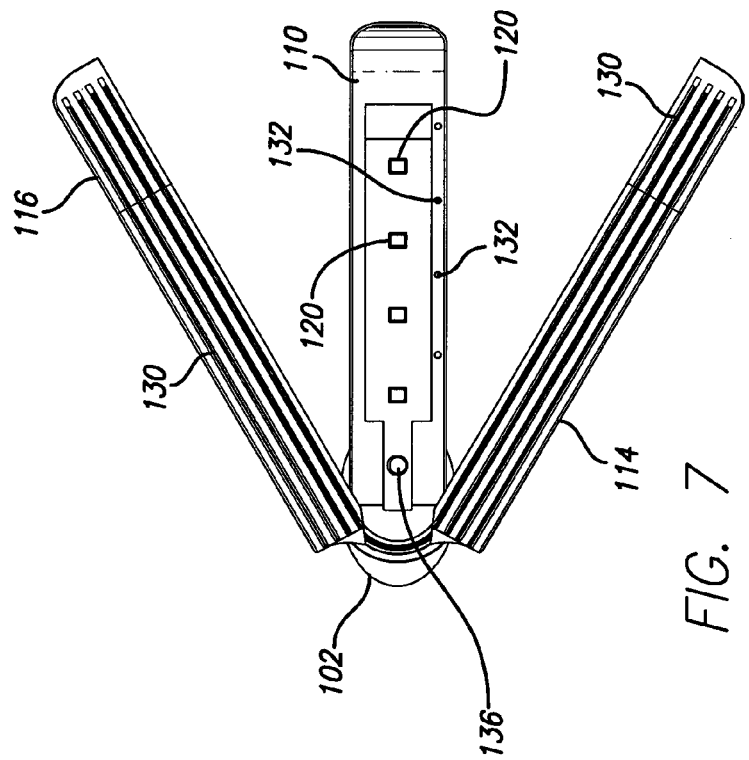
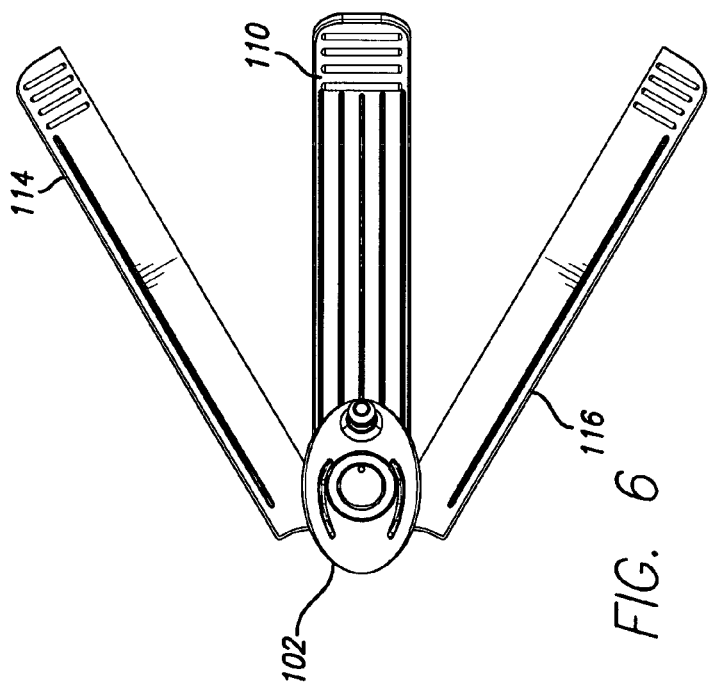
FIG. 7
FIG. 6

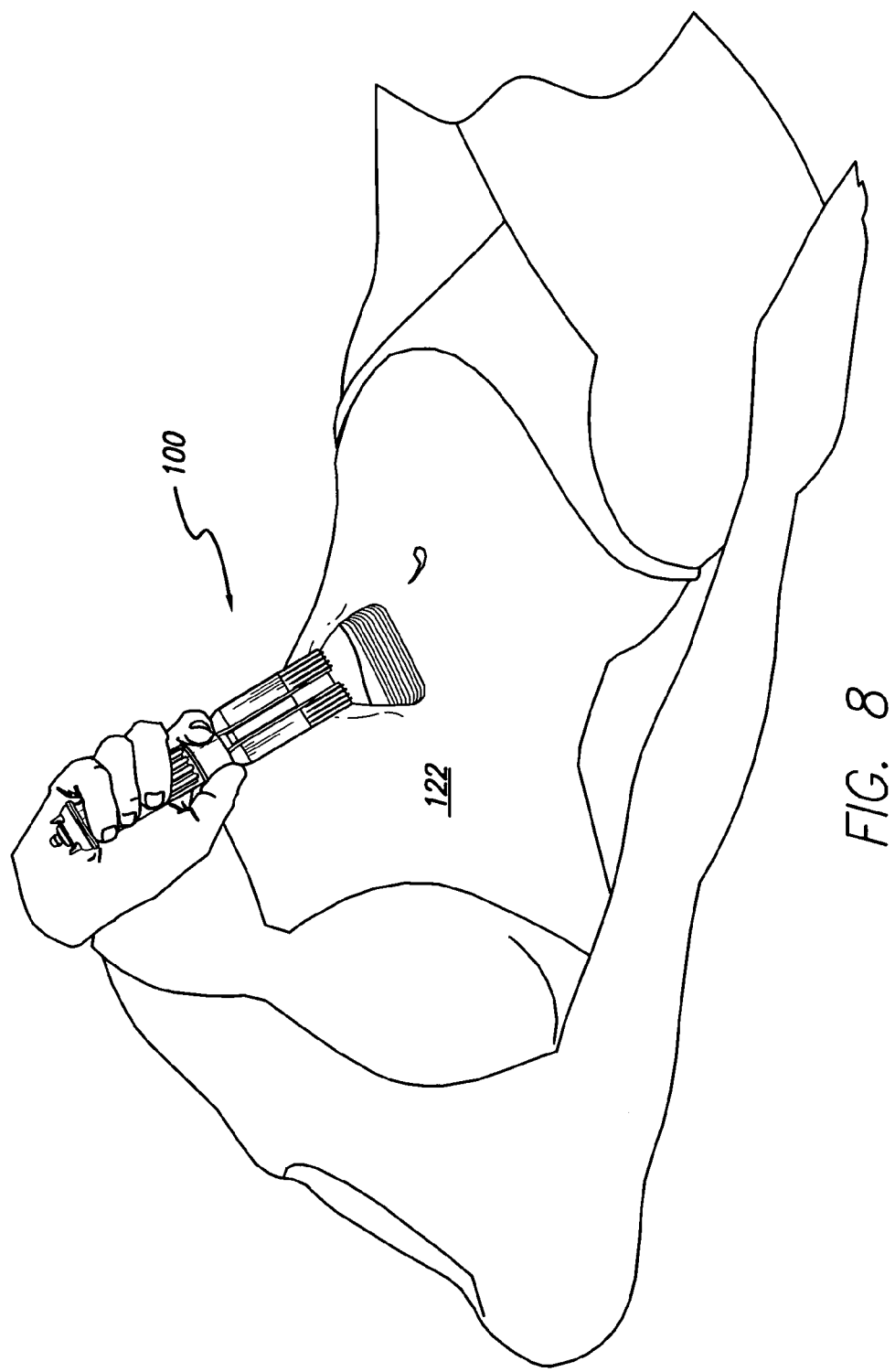

US 8,012,089 B2

DISPOSABLE EXPANDABLE CORDLESS LIGHTED RETRACTOR

CROSS-REFERENCES TO RELATED APPLICATIONS

This patent application is a continuation-in-part and claims the benefit of U.S. patent application Ser. No. 11/439,316 filed May 22, 2006 now U.S. Pat. No. 7,384,392 for Disposable Expandable Cordless Lighted Retractor, which application is incorporated by this reference.

TECHNICAL FIELD

This invention relates to surgical instruments used to manipulate a patient's tissues, such as skin, bone, and muscle.

BACKGROUND ART

Surgical retractors and expanders are used to manipulate a patient's tissues, such as skin, muscle, or bone, and are commonly utilized by surgeons and dentists on the human body and by veterinarians on animals. Retractors have blades that tend to pull the tissue to create more room for a surgeon to view an area of interest, such as a body cavity, and to manipulate other surgical tools. Expanders perform a similar function by tending to push the tissue instead of pulling it. Retractors and expanders are available in a variety of blade sizes and shapes to pull and push different body tissues in different locations on the body. For example, the blade can be curved to lift or separate a portion of the patient's tissues. When both retraction and expansion are needed, a surgeon commonly uses a separate device for each function. This further crowds the patient's body cavity and often requires additional operating assistants to manipulate and hold each device.

While manipulating the patient's tissues, it is important to adequately illuminate the corresponding region of the patient's body. As ambient light is not always sufficient to light a body cavity, illumination is commonly accomplished by a separate light. This light generally must then be held in place near the body cavity by an operating assistant or by some sort of rigging, further crowding the surgical area.

To provide illumination, existing devices may also include a fiber optic bundle to transmit light from a light source to the body cavity of the patient. Such systems, however, also have many drawbacks. For example, the light source often has a limited life and a poor distribution over time. At the end of its life cycle, the light system's components are typically expensive to replace. In addition, the bundle is cumbersome since it often drags on the surgeon and impedes the surgeon's movements. Moreover, the bundle may become de-sterilized due to movement of the surgical staff.

Furthermore, many of the existing devices must be sterilized between uses, a process that may be expensive and time-consuming. Moreover, procedures to sterilize the device may also damage it. Even with sterilization procedures, however, there remains a risk of pathogen cross infection because the instrument will be used more than once. As such, the re-sterilized device will never be as good as new. In addition, there may be other maintenance and extended warranty issues that are not present with a single-use, disposable device.

Existing instruments are also often made of metal. As such, they are difficult to hold for long periods of time since their weight induces fatigue in the surgeon's hands and arms. This is exacerbated by the typical handle design, which is often not ergonomic. Moreover, the metal conducts electricity, which can present an additional risk to the patient and surgeon, such as by electrosurgical burns.

In a typical breast augmentation procedure, for example, a three to six centimeter (3-6 cm) incision is made adjacent the patient's breast. A retractor then holds the tissue up, and an electrocautery tool forms a cavity. An implant is then placed above or below the pectoralis muscle, under the breast tissue.

Existing devices used to perform the breast augmentation procedure include the Accurate Surgical & Scientific Instruments Corporation (ASSI) breast retractor and the Stanger C circular breast retractor (also from ASSI), along with a fiber-optic light source and a suction source. However, the light and suction are only at the end of the device; so light and suction are limited to the end of the device and do not affect the entire breast pocket.

There is therefore a need for a surgical instrument that combines the functions of retraction, expansion, and illumination into a single device while remaining lightweight and easy to handle. There is further a need for such an instrument to be disposable after a single use, yet remain economical. Additionally, there is a need for a light source that illuminates the entire cavity, is cordless, and does not require cumbersome fiber optics. There is also a need for a surgical instrument that provides suction throughout the cavity and is not limited to the end of the device.

DISCLOSURE OF INVENTION

The objects discussed above are provided by the surgical instrument of the present invention. In one aspect of the invention, a hand-held, surgical instrument to manipulate a patient's tissues has a grip, a first blade, a second blade, a blade actuator, at least one blade rib on the first blade or the second blade, a light, and a power source.

The first blade extends from the base end of the grip. The second blade also extends from the base end of the grip and is divided longitudinally into a left segment and a right segment. The left segment and the right segment are each pivotable about a common axis.

The blade actuator is connected to the second blade, and movement of the blade actuator causes the segments of the second blade to pivot about the common axis to manipulate the patient's tissues.

The light is connected to the first blade and illuminates the patient's tissues proximate the first blade. The power source is within the grip and is in electrical communication with the light.

In another aspect of the invention, the surgical instrument includes a suction connector connected to a suction channel that is internal to the surgical instrument, where the suction connector is shaped and dimensioned to permit connection to a suction tube. This version of the invention may also include a plurality of suction ports on the underside of the first blade. Each of the plurality of suction ports is connected to the suction connector by the suction channel.

The blade rib may include a plurality of longitudinal blade ribs extending along the length of the first blade, the second blade, or both. The blade rib may also include a plurality of transverse blade ribs extending along the width of the first blade, the second blade, or both.

In a further aspect of the invention, the surgical instrument includes a camera that is integral to the surgical instrument and provides images of the patient's tissues. Such versions may also include a transmitter connected to wirelessly transmit the camera images to a separate display.

BRIEF DESCRIPTION OF DRAWINGS

FIG. 6 is a bottom view of an embodiment of a surgical instrument, showing an extended position.

FIG. 7 is a depiction of how a surgical instrument in accordance with the present invention might be used.

FIG. 8 is a depiction of how a surgical instrument in accordance with the present invention might be used.

BEST MODE FOR CARRYING OUT THE INVENTION

Figure 1:
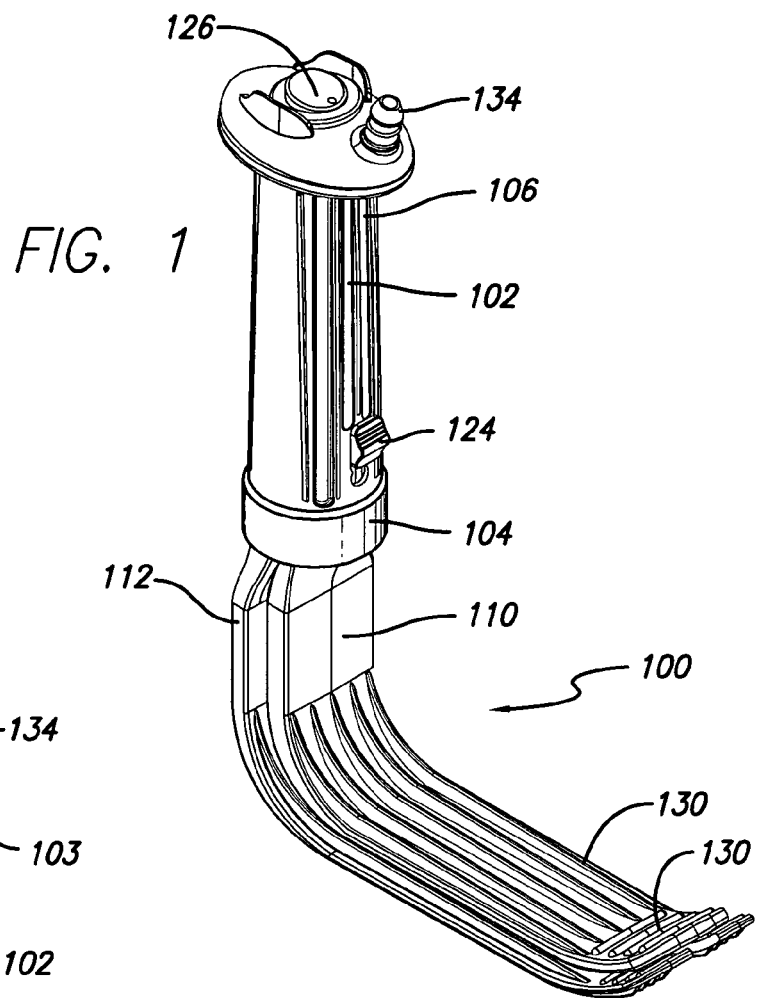
FIG. 1 is a perspective view of an embodiment of a surgical instrument in accordance with the present invention, showing a retracted position.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Referring to the accompanying figures, a surgical instrument 100 allows a user to manipulate and illuminate a patient's tissues 122. The manipulation, for example, may be expansion or retraction of the patient's skin, muscle, or bone. Expansion and retraction may also be performed simultaneously. Depending on the embodiment utilized, the surgical instrument 100 may be used to perform surgery on the breast, such as gynecomastia correction; augmentation, for example, by subpectoral or submammary pockets; mastopexy; reduction; tissue expansion; and subcutaneous mastectomy prior to breast reconstruction. The device allows for a conservative sized incision for introduction, removal, or replacement of an implant. It also facilitates visualization for effective hemostasis in the breast pocket and dissection of the periphery of the breast pocket. Additionally, the surgical instrument 100 may be used to perform surgery on a patient's abdomen, pelvis, or trunk and limbs, such as dissection of a pedicled or free flap, like a latissimus dorsi muscle for reconstruction. With the possible exception of a suction tube, the surgical instrument 100 is completely detached, cordless, and wireless.

The surgical instrument 100 has a handle 102, a first blade 110, a second blade 112, and a blade actuator 124. The surgical instrument 100 preferably also includes a light 120, a power source 128, and a light switch 126.

The handle 102 is preferably configured to be hand-held and may have a grip handle, cylindrical grip, or other ergonomic design to be held by a user. In some embodiments, the handle 102 has protrusions such as vertical or horizontal ridges, to facilitate comfortable holding by the user. In a version of the invention, the handle 102 has a flared top 103 to allow the handle 102 to be more easily gripped and held. It is further contemplated that the handle 102 may be made of a soft, foam plastic material to provide a comfortable, resilient grip. In some embodiments, the handle 102 is shaped to permit connection to a holding device or other device for mounting the surgical instrument to a surgical table or to a floor stand.

Preferably, the surgical instrument 100 is composed of materials permitting it to be readily and economically disposable. For example, the handle 102, the first blade 110, and the second blade 112 may each be made of a plastic polymer. The plastic polymer is preferably a lightweight, medical grade polymer and most preferably is a polycarbonate. Lightweight materials also permit the surgeon to use the device over long periods of time with less fatigue.

Figure 2:
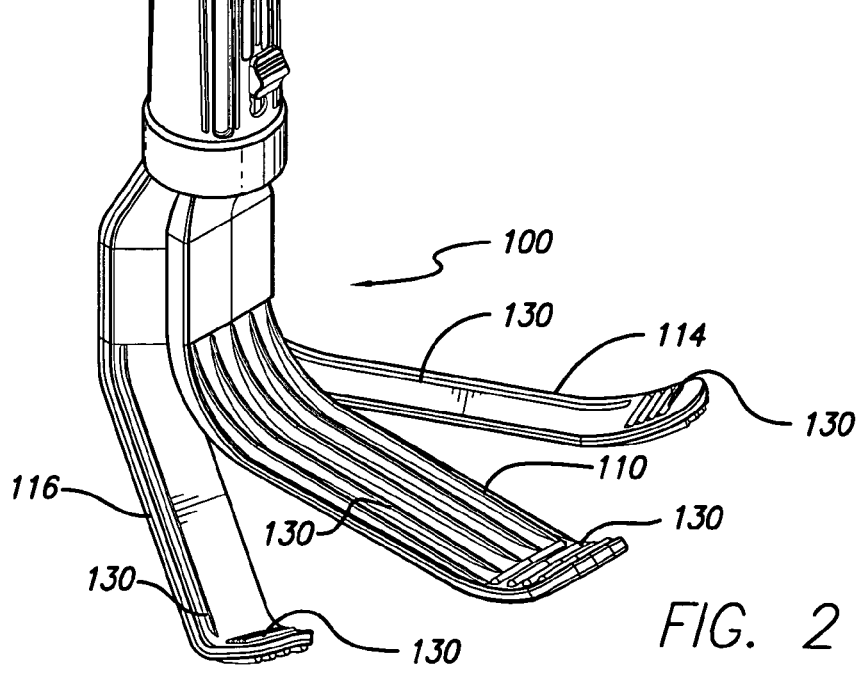
FIG. 2 is a perspective view of an embodiment of a surgical instrument, showing an extended position.
Figure 3:
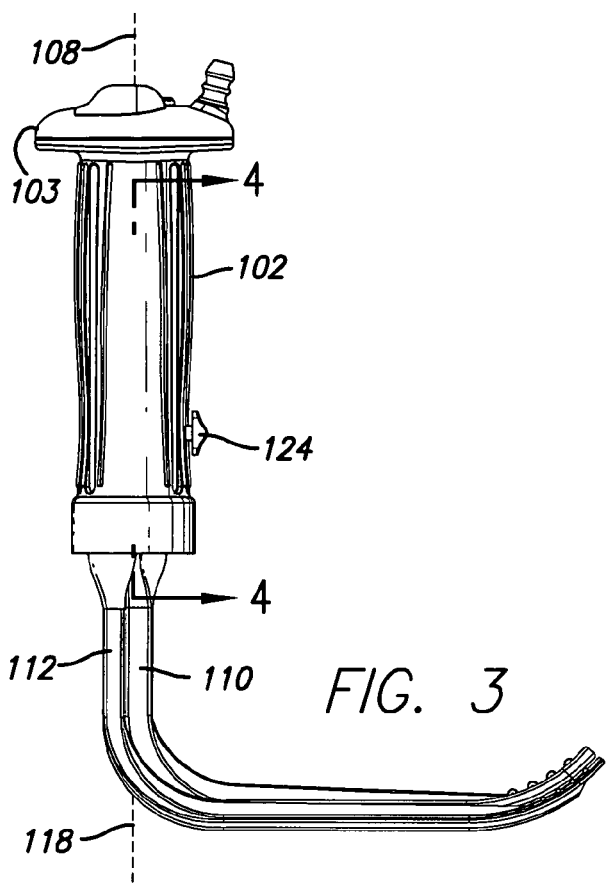
FIG. 3 is a side view of an embodiment of a surgical instrument.

The first blade 110 extends from the base end 104 of the handle 102 and may be generally flat and generally rectangular in profile, such as shown in FIG. 1 and FIG. 2. However, it is equally contemplated that other blade profiles or cross-sections sufficient to manipulate the patient's tissues may be used, such as cylindrical, paddle-shaped, rectangular, or conical. In some embodiments, at least a portion of the length of the first blade 110 is generally oblique to the handle 102. In the depicted embodiments, the first blade 110 is generally perpendicular to the handle 102. It is equally contemplated that the first blade 110 could be at any angle to the handle 102, and it is contemplated that the angle may be adjustable, such as by inclusion of a hinge in the blade or at the attachment point of the blade with the handle 102.

In some embodiments, the first blade 110 is ribbed or ridged to add structural integrity and increased strength to the blade. Preferably, this is accomplished by including one or more blade ribs 130. The blade ribs 130 also improve the ability of the blade to grasp and control the patient's tissues 122. One or more blade ribs 130 preferably extend longitudinally along the length of the blade, and one or more blade ribs 130 are preferably at the tip of the blade and positioned transversely to the length of the blade. Examples of such longitudinal and transverse blade ribs 130 are shown in FIG. 1 and FIG. 2.

In some embodiments, the first blade 110 has a flared tip, where the tip is oblique to the adjacent portion of the blade, such as shown in FIG. 1 and FIG. 2. Such a flared tip facilitates movement of the tip among the patient's tissues 122. In some embodiments, the first blade 110 has tines, or teeth, at the tip to grip or maneuver the tissues. It is further contemplated that, in some versions the first blade 110 is extendable or adjustable. In such embodiments, the length or width of the blade may be made longer or shorter, for example, by sliding one portion of the blade relative to another portion.

The second blade 112 also extends from the base end 104 of the handle 102, may be generally flat, generally rectangular in profile, and may have at least a portion of its length generally oblique to the handle. It is equally contemplated that the second blade 112 could be at any angle to the handle 102, and it is contemplated that the angle may be adjustable, such as by inclusion of a hinge at a bend in the blade or at the attachment point of the blade with the handle 102. As with the first blade 110, additional blade profiles and cross-sections are equally contemplated by the invention, and the second blade 112 may be ribbed or ridged, such as by the inclusion of one or more blade ribs 130, as described for the first blade 110. In some embodiments, the second blade 112 may have a flared tip, like what is shown in FIG. 1 and FIG. 2. In some versions of the invention, the second blade 112 may have tines, or teeth, instead of a rounded tip. In some embodiments, the first blade 110 may have tines, or teeth, at the tip to grip or maneuver the tissues. It is further contemplated that the second blade 112 is extendable or adjustable. In such embodiments, the length or width of the blade may be made longer or shorter, for example, by sliding one portion of the blade relative to another portion.

The second blade 112 is divided, for example longitudinally, into a left segment 114 and a right segment 116. The left segment 114 and right segment 116 are in pivotal relation to each other. Preferably, the left segment 114 and right segment 116 are each rotatable about the base end 104 of the handle 102, where the axis of pivoting 118 is generally along, or collinear to, the centerline 108 of the handle 102.

In the embodiment shown in FIG. 2, the second blade 112 is positioned just below the first blade 110 in a preferred arrangement. The present invention, however, contemplates other such configurations, such as positioning the second blade 112 just above the first blade 110 or positioning the left segment 114 and right segment 116 on either side of the first blade 110. It is further contemplated that embodiments of the invention may have more than two blades, and it is contemplated that the blades may not be on the same side of the handle. For example, a blade might be at an angle, such as 90° or 180°, to another blade.

The blade actuator 124 positions the left segment 114 and right segment 116 of the second blade 112. Movement of the blade actuator 124 to a first position causes the segments of the second blade 112 to pivot such that the left segment 114 and the right segment 116 are separated, defining an extended position of the second blade. Such an extended position is depicted in FIG. 2. Movement of the blade actuator 124 to a second position causes the segments of the second blade 112 to pivot such that the left segment 114 and the right segment 116 come together, defining a retracted position of the second blade. Such a retracted position is depicted in FIG. 1. Furthermore, in some embodiments a plurality of positions between the retracted position and the extended position are achievable by positioning the blade actuator 124 in a plurality of positions intermediate the first position and the second position. In the embodiment depicted in FIG. 1, the second blade 112 is generally parallel to the first blade 110 when the second blade 112 is in the retracted position.

The blade actuator 124 may be located on the handle 102 and may include a sliding switch. In an embodiment of the invention, the blade actuator 124 may be locked into the first position, the second position, or any one of the plurality of intermediate positions. The locking mechanism may be in the form of one or more detents to engage and hold the blade actuator 124 in the selected position. For example, the detents may be recesses into which the blade actuator 124 can be moved and held in place. The blade actuator 124, in some embodiments, may position the left segment 114 and right segment 116 of the second blade 112 by translating the motion of the blade actuator 124 to the segments by way of a cam and follower, gear arrangement (such as a rack and pinion), four-bar mechanism, lever, electric motor, hydraulic or pneumatic actuator, or other method known in the art.

The light 120 may include at least one light emitting diode (LED). The light 120 illuminates the patient's tissues 122 immediately adjacent to or proximate the blades. Although the light 120 may be at the base end 104 of the handle 102, preferably the light 120 is located on at least one of the first blade 110 or the second blade 112. More preferably, the light 120 is located on the underside of the first blade 110 and is a plurality of light emitting diodes, such as depicted in FIG. 6. It is further contemplated that the light 120 may be located within the profile of the blade. In such embodiments, the portion of the blade near the light 120 is constructed of a translucent or transparent material to allow the light to pass through the blade to illuminate the patient's tissues. Preferably, the light 120 is electrically and thermally insulated from the patient's tissues 120.

The surgical instrument 100 as described is strong, is lightweight, and provides light distribution along the entire length of the blade. In addition, for embodiments where each LED is completely insulated, there is no risk of electrocautery burn to the skin or breast tissue of the patient.

Figure 4:
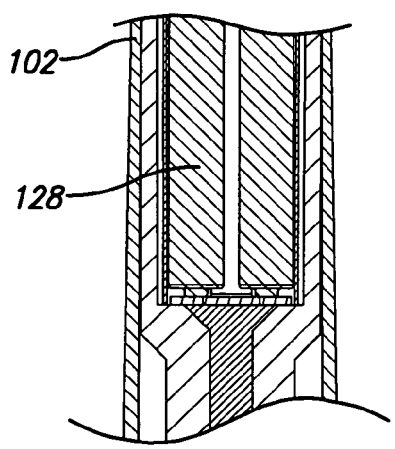
FIG. 4 is a partial cutaway of a portion of the handle of an embodiment of a surgical instrument.
Figure 5:
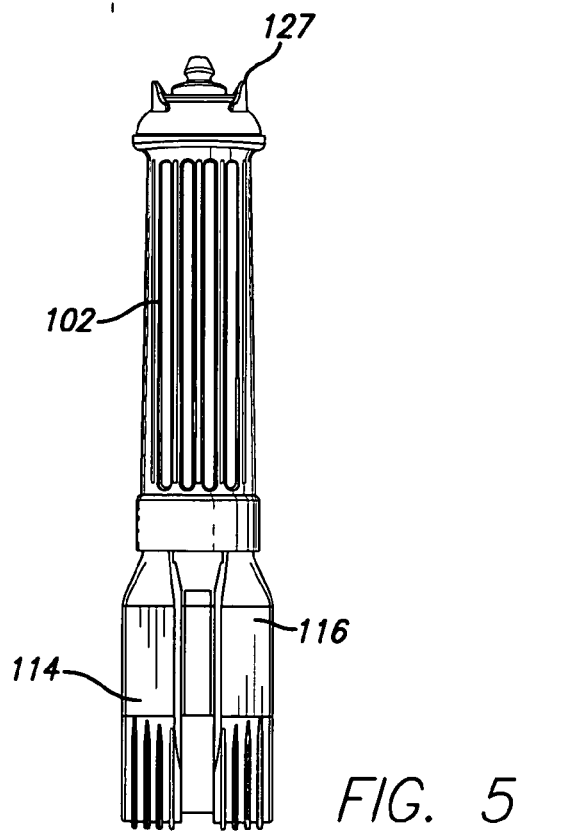
FIG. 5 is a rear view of an embodiment of a surgical instrument.
Figure 9:
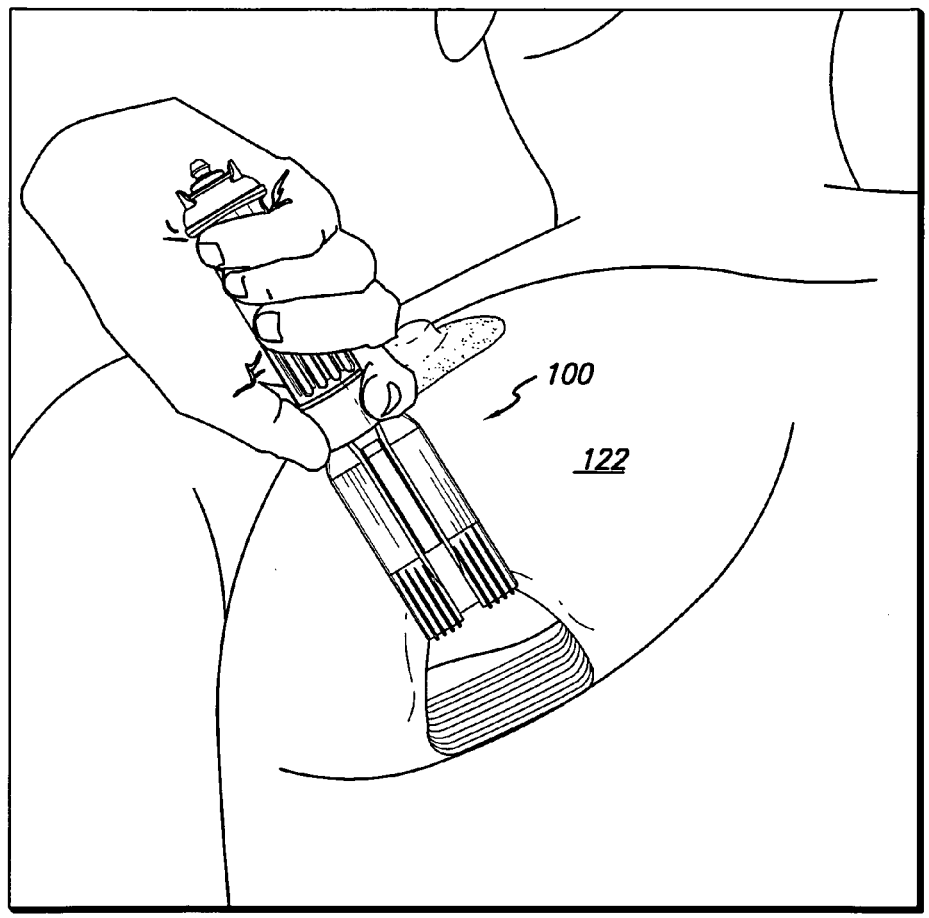
FIG. 9 is another depiction of how a surgical instrument in accordance with the present invention might be used.

The power source 128 may be located within the handle 102 and may include at least one battery, preferably two AAA-sized batteries. See, for example, FIG. 4. Such batteries generally allow the surgical instrument 100 to function for up to five hours. As a typical breast augmentation surgery lasts about one hour and other typical surgeries last three to four hours, a five hour battery life is normally sufficient. Other power sources are also usable, though it is preferred that such sources be readily removable from the surgical instrument 100 or be disposable so as to permit the surgical instrument 100 to be economically disposable.

In addition, there may be a light switch 126 to interrupt and reestablish the electrical communication between the power source 128 and the light 120. The light switch 126 is preferably a toggle switch located at the top end 106 of the handle 102. It is also contemplated that the light switch 126 be a dial or sliding switch. The light switch 126 may be used to select a low level of emitted light, a high level, and at least one level between the low level and the high level. In some versions, the handle 102 includes one or more switch guards 127 to minimize inadvertent use of the light switch 126. The switch guard 127 may, for example, be one or more raised portions of the handle 102 adjacent the light switch 126.

It is also contemplated that the handle 102 may have a channel or tube extending through it to one or both of the first blade 110 and second blade 112. The channel or tube can be connected to a suction device, such as a suction tap in an operating room, to provide aspiration of gas or fluid from the region of the patient's tissues adjacent to the surgical instrument 100. In addition, the first blade 110, the second blade 112, or both may include one or more suction ports 132. Preferably, a plurality of suction ports 132 is located on the underside of the first blade 110, providing suction along the entire length of the blade. An example of an array of suction ports is shown in FIG. 6. Such suction is particularly useful for aspirating cauterization smoke throughout the breast cavity. In embodiments having one or more suction ports 132, the handle 102 preferably includes a suction connector 134 for connecting the suction ports 132 to a standard suction source (such as via a standard suction tube).

A version of the surgical instrument 100 includes a camera 136 and a wireless transmitter to transmit images from the patient's body cavity to a separate display. In such embodiments, the wireless transmitter may be located within the handle 102. Such a version is particularly useful for teaching how to perform a surgical procedure. Some embodiments may include wireless technology such as that available from BLUETOOTH® SIG, Inc., a Delaware U.S.A. corporation.

While the present invention has been described with regard to particular embodiments, it is recognized that additional variations of the present invention may be devised without departing from the inventive concept. For example, while the depicted embodiments are suitable for manipulation of the tissues of a human being, particularly during plastic surgeries such as breast augmentation, it is equally contemplated that the surgical instrument may be used for other surgical procedures and on other regions of the patient's body. It is furthermore contemplated that the surgical instrument may be used by persons such as veterinary surgeons to manipulate the tissues of animals.

INDUSTRIAL APPLICABILITY

This invention may be industrially applied to the development, manufacture, and use of surgical instruments used to manipulate a patient's tissues, such as skin, bone, and muscle.

What is claimed is:

1. A hand-held, disposable, surgical instrument to manipulate a patient's tissues, comprising:
    (a) a grip handle, shaped and dimensioned to be held by a user's hand and having a base end, a top end, and a centerline, the grip handle comprising a polycarbonate, the top end being flared to permit the grip handle to be more easily gripped and held by the user;
    (b) a first blade extending from the base end of the grip handle and having an underside, the blade being generally flat and having at least a portion of its length generally perpendicular to the grip handle, the first blade having a first blade tip opposite the base end of the grip handle, the first blade comprising a polycarbonate;
    (c) a second blade extending from the base end of the grip handle, the blade being generally flat and having at least a portion of its length generally perpendicular to the grip handle, the second blade being divided longitudinally into a left segment and a right segment, the left segment and the right segment each being pivotable about the base end of the grip handle, the axis of pivoting being generally collinear with the centerline of the grip handle, the second blade having a second blade tip opposite the base end of the grip handle, the second blade comprising a polycarbonate;
    (d) a blade actuator on the grip handle, the blade actuator comprising a sliding switch, whereby movement of the sliding switch to a first position causes the segments of the second blade to pivot about the base end of the grip handle such that the left segment and the right segment are separated, thereby defining an expanded position of the second blade, whereby movement of the sliding switch to a second position causes the segments of the second blade to pivot about the base end of the grip handle such that the left segment and the right segment come together, thereby defining a retracted position of the second blade, the second blade being generally parallel to the first blade when the second blade is in the retracted position;
    (e) a plurality of light emitting diodes (LEDs) on the underside of the first blade;
    (f) a power source within the grip handle and in electrical communication with the plurality of LEDs, the power source comprising at least one battery;
    (g) a light switch at the top end of the grip handle to interrupt and reestablish the electrical communication between the power supply and the plurality of LEDs;
    (h) a switch guard at the top end of the grip handle proximate the light switch, the switch guard comprising a raised portion of the grip handle that is shaped and dimensioned to minimize inadvertent use of the light switch by the user;
    (i) a suction connector at the top end of the grip handle, the suction connector being shaped and dimensioned to permit to connection to a suction tube;
    (j) a plurality of suction ports on the underside of the first blade, each of the plurality of suction ports being connected to the suction connector by a suction channel internal to the surgical instrument;
    (k) a first plurality of longitudinal blade ribs rising from the generally flat first blade and extending along the length of the first blade;
    (l) a second plurality of longitudinal blade ribs rising from the generally flat second blade and extending along the length of the second blade;
    (m) a first plurality of transverse blade ribs rising from the generally flat first blade and extending along the width of the first blade at the first blade tip; and
    (n) a second plurality of transverse blade ribs rising from the generally flat second blade and extending along the width of the second blade at the second blade tip.

2. The surgical instrument of claim 1 further comprising a camera and a wireless transmitter, the camera connected to the first blade to provide images of the patient's tissues, the wireless transmitter being within the grip handle to wirelessly transmit the images to a display.

* * * * *